United States Patent [19]

Reiser et al.

[11] 4,435,411

[45] Mar. 6, 1984

[54] COMBATING FUNGI WITH 1-PHENYL-2-(1,2,4-TRIAZOL-1-YL)-PROP-2-EN-1-ONES

[75] Inventors: Wolf Reiser; Hans-Ludwig Elbe, both of Wuppertal; Karl Büchel, Burscheid; Paul-Ernst Frohberger, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 259,304

[22] Filed: Apr. 30, 1981

[30] Foreign Application Priority Data

May 19, 1980 [DE] Fed. Rep. of Germany ....... 3019045

[51] Int. Cl.³ .................. A01N 43/64; C07D 249/08; C07F 1/08
[52] U.S. Cl. ..................................... 424/269; 424/232; 424/245; 542/400; 542/429; 542/458; 542/468; 542/470; 548/101; 548/262
[58] Field of Search ................ 548/262, 101; 542/458, 542/400, 468; 424/245, 269

[56] References Cited

U.S. PATENT DOCUMENTS 4,086,351 4/1978 Balasabramanyan et al. ...... 548/262
4,182,862 1/1980 Chan ................................. 548/262

FOREIGN PATENT DOCUMENTS 2645617 4/1977 Fed. Rep. of Germany ...... 548/262
15387 9/1980 European Pat. Off. ............ 424/269
24538 3/1981 European Pat. Off. ............ 542/458

Primary Examiner—Alton D. Rollins
Attorney, Agent, or Firm—Sprung, Horn, Kramer & Woods

[57] ABSTRACT

A 1-phenyl-2-(1,2,4-triazol-1-yl)-prop-2-en-1-one of the formula

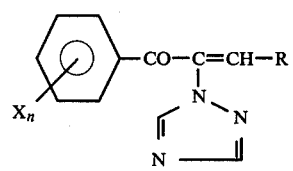

in which
R is methyl, ethyl, isopropyl, alkyl with more than 3 carbon atoms, optionally substituted cycloalkyl, optionally substituted cycloalkenyl, optionally substituted alkenyl, optionally substituted alkynyl, optionally substituted phenoxyphenyl, or phenylalkyl which is optionally substituted in the alkyl part and/or in the phenyl part,
X each independently is halogen, optionally substituted phenyl or optionally substituted phenoxy, and
n is 0, 1, 2 or 3, or an addition product thereof with a physiologically acceptable acid or a metal salt which possesses fungicidal activity.

10 Claims, No Drawings

COMBATING FUNGI WITH 1-PHENYL-2-(1,2,4-TRIAZOL-1-YL)-PROP-2-EN-1-ONES

The present invention relates to certain new substituted phenyl triazolyl-vinyl ketones, to a process for their preparation and to their use as fungicides.

It has already been disclosed that substituted phenacyl-triazolyl-styrene derivatives, such as, in particular, 1-(2,4-dichlorophenacyl)-1-(1,2,4-triazol-1-yl)-styrene derivatives, have a good fungicidal activity (see DE-OS (German Published Specification) No. 2,645,617). However, the action of these compounds is not always completely satisfactory, especially when small amounts and low concentrations are applied.

The present invention now provides, as new compounds, the substituted phenyl triazolyl-vinyl ketones of the general formula

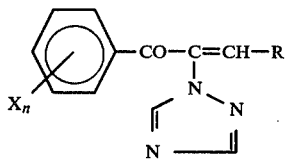
(I)

in which
  R represents methyl, ethyl, isopropyl, alkyl with more than 3 carbon atoms, optionally substituted cycloalkyl, optionally substituted cycloalkenyl, optionally substituted alkenyl, optionally substituted alkynyl, optionally substituted phenoxyphenyl or phenylalkyl which is optionally substituted in the alkyl part and/or in the phenyl part,
  X represents halogen, optionally substituted phenyl or optionally substituted phenoxy and
  n represents 0, 1, 2 or 3, each X being selected independently when n is 2 or 3,
and physiologically acceptable acid addition salts and metal salt complexes thereof.

The compounds of the formula (I) can exist in two geometric isomer forms (E-form and Z-form), depending on the arrangement of the groups bonded to the double bond; they are preferentially obtained in a varying E/Z-isomer ratio. The formula (I) embraces both the individual isomers and the isomer mixtures.

The invention also provides a process for the preparation of a substituted phenyl triazolyl-vinyl ketone of the general formula (I) in which
  (a) a keto-enamine of the general formula

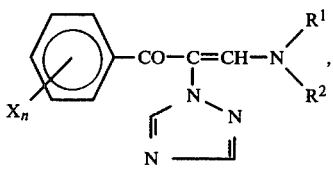
(II)

in which
  X and n have the abovementioned meanings and
  $R^1$ and $R^2$ are identical or different and represent alkyl,
is reacted with an organo-magnesium compound of the general formula Hal—R     (III), in which
  R has the abovementioned meaning and
  Hal represents halogen,
in the presence of a solvent and, if appropriate, in the presence of a catalyst, or
  (b) a triazolyl ketone of the general formula

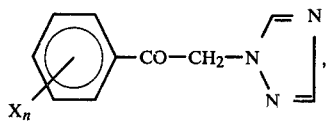
(IV)

in which
  X and n have the abovementioned meanings,
is reacted with an aldehyde of the general formula

O=CH—R     (V), in which
  R has the abovementioned meaning,
in the presence of a solvent and in the presence of a catalyst.

If appropriate, an acid or a metal salt can be added onto the compound of the formula (I) thus obtained.

The substituted phenyl triazolyl-vinyl ketones of the formula (I) have powerful fungicidal properties. Surprisingly, the compounds according to the invention exhibit a better fungicidal activity than the 1-(2,4-dichlorophenacyl)-1-(1,2,4-triazol-1-yl)-styrene derivatives known from the state of the art, which are closely related compounds chemically and from the point of view of their action. The substances according to the invention thus represent an enrichment of the art.

The formula (I) provides a general definition of the substituted phenyl triazolyl-vinyl ketones according to the invention. Preferably, in this formula,
  R represents methyl, ethyl, isopropyl or straight-chain or branched alkyl with 4 to 29 (especially up to 18) carbon atoms; cycloalkyl or cycloalkenyl, in either case with 5 to 7 carbon atoms, either of which may be optionally substituted by alkyl with 1 to 4 carbon atoms; straight-chain or branched alkenyl or alkynyl with in either case up to 6 carbon atoms, either of which optionally carries one or more substituents selected from hydroxyl, alkoxy with 1 to 4 carbon atoms and phenyl, which can optionally be substituted by halogen or alkyl with 1 to 4 carbon atoms; phenoxyphenyl, optionally substituted by halogen and/or by alkyl with 1 to 4 carbon atoms; or phenalkyl with 1 to 4 carbon atoms in the alkyl part (especially benzyl), which optionally carries one or more substituents on the phenyl selected from halogen, alkyl with 1 to 4 carbon atoms and halogenoalkyl with 1 to 4 carbon atoms and 1 to 5 identical or different halogen atoms (especially fluorine and chlorine atoms) and which optionally carries one or more substituents on the alkyl selected from cyano, hydroxycarbonyl and alkoxy-carbonyl with 1 to 4 carbon atoms in the alkyl part; and
  X represents halogen or phenyl or phenoxy, either of which may optionally carry one or more substituents selected from halogen, alkyl with 1 to 4 carbon atoms and halogenoalkyl with 1 to 4 carbon atoms and 1 to 5 identical or different halogen atoms (especially fluorine and chlorine atoms).

Particularly preferred compounds of the formula (I) are those in which R represents cyclohexyl, cyclohexenyl, cyclopentyl or cyclopentenyl, in each case optionally substituted by methyl or ethyl; or methacryl, trimethylvinyl, acetylenyl, hydroxyacetylenyl, methoxyacetylenyl, phenacetylenyl, chlorophenylacetylenyl, propargyl, hydroxypropargyl, methoxypropargyl, phenylpropargyl or chlorophenylpropargyl; or benzyl which is optionally substituted in the phenyl part by fluorine, chlorine or methyl, it being possible for the —CH$_2$— group also to be substituted by cyano, hydroxycarbonyl or methoxycarbonyl; or phenoxyphenyl which is optionally substituted by fluorine, chlorine or methyl; X represents fluorine, chlorine or bromine; or phenyl or phenoxy, either of which is optionally substituted by fluorine, chlorine, bromine, methyl, ethyl, isopropyl or tert.-butyl; and n represents 0, 1 to 2.

If, for example, 1-(2,4-dichlorophenyl)-4-dimethylamino-2-(1,2,4-triazol-1-yl)-2-propen-1-one and phenylacetylene-magnesium bromide are used as starting materials in process variant (a), the course of the reaction can be represented by the following equation:

formula (IV) with amideacetals or aminal esters of the general formula

or

in which

R$^1$ and R$^2$ have the abovementioned meanings and
R$^3$ represents alkyl with 1 to 4 carbon atoms, in a manner which is in itself known in the presence of an inert organic solvent, for example an aromatic hydrocarbon or, in particular, an excess of the amide-acetal or aminal ester of the formula (VIa) or (VIb)

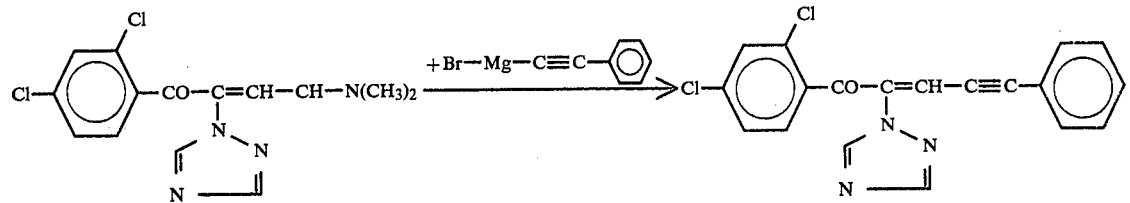

If, for example, α-(1,2,4-triazol-1-yl)-2,4-dichloroacetophenone and cyclohexanecarbaldehyde are used as starting materials in process variant (b), the course of the reaction can be represented by the following equation:

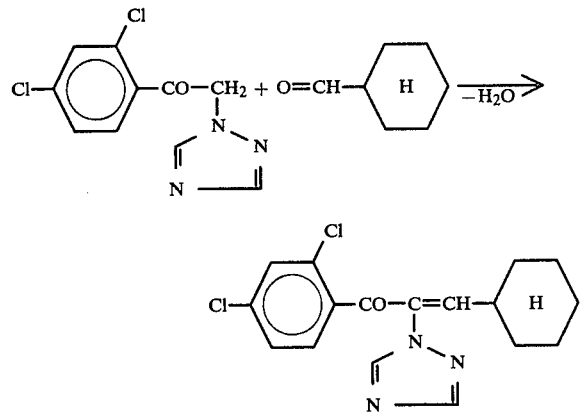

The formula (II) provides a general definition of the keto-enamines to be used as starting materials for process variant (a). In this formula, X and n preferably have those meanings which have already been mentioned as preferred in connection with the description of the substances of the formula (I). R$^1$ and R$^2$ are identical or different and preferably represent alkyl with 1 to 4 carbon atoms, especially methyl.

The keto-enamines of the formula (II) are disclosed in application Ser. No. 219,154, filed Dec. 22, 1980, now U.S. Pat. No. 4,380,628. The keto-enamines of the formula (II) can be obtained by the processes described in that application, by reacting triazolyl-ketones of the employed, at the boiling point (in this context, see also Chem.Ber. 101, 41–50 (1968); J. Org. Chem. 43, 4248–50 (1978) and the preparative examples herein).

The amide-acetals and aminal esters of the formulae (VIa) and (VIb) are generally known compounds of organic chemistry (see, for example, Chem.Ber. 101, 41–50 (1968) and J. Org. Chem. 43, 4248–50 (1978)).

The formula (III) provides a general definition of the organo-magnesium compounds also to be used as starting materials for the reaction in process variant (a). In this formula, R preferably represents those radicals which have already been mentioned as preferred in connection with the description of the substances of the formula (I). Hal preferably represents chlorine or bromine.

The formula (IV) provides a general definition of the triazolyl-ketones to be used as starting materials for process variant (b). In this formula, X and n preferably have those meanings which have already been mentioned as preferred in connection with the description of the substances of the formula (I).

The triazolyl-ketones of the formula (IV) are known (see, for example, U.S. Ser. No. 792,756, filed May 22, 1977, DE-OS (German Published Specification) No. 2,610,022 and DE-OS (German Specification) No. 2,638,470); they can be prepared by customary methods, by reacting the corresponding halogenoketones with 1,2,4-triazole in the presence of an acid-binding agent.

The formula (V) provides a general definition of the aldehydes also to be used as starting materials for process variant (b). In this formula, R preferably represents those radicals which have already been mentioned as preferred in connection with the description of the substances of the formula (I).

The aldehydes of the formula (V) are generally known compounds of organic chemistry.

Preferred solvents for the reaction in process variant (a) are inert organic solvents in pure form or in mixtures. These include, as preferences, ethers, such as diethyl ether, methyl ethyl ether, tetrahydrofuran or dioxane; aliphatic and aromatic hydrocarbons, such as benzene, toluene or xylene; and hexamethylphosphoric acid triamide.

The reaction temperatures can be varied within a relatively wide range in carrying out process variant (a). In general, the reaction is carried out at between $-50°$ and $+150°$ C., preferably at between $-20°$ and $+120°$ C.

The reaction in process variant (a) can be carried out in the presence of an inert gas, for example nitrogen or helium.

In carrying out process variant (a), 1 to 1.5 moles of organo-magnesium compound of the formula (III) are preferably employed per mole of keto-enamine of the formula (II). The compounds of the formula (I) are isolated in the customary manner.

Preferred solvents for process variant (b) are inert organic solvents. These include, as preferences, alcohols, such as methanol and ethanol; ethers, such as tetrahydrofuran and dioxane; aliphatic and cycloaliphatic hydrocarbons, such as hexane and cyclohexane; aromatic hydrocarbons, such as benzene, toluene and cumene; and halogenated aliphatic and aromatic hydrocarbons, such as methylene chloride, carbon tetrachloride, chloroform, chlorobenzene and disclorobenzene.

Process variant (b) is carried out in the presence of a catalyst. Any of the acid and, in particular, basic catalysts which can customarily be used, and buffer mixtures thereof, can be employed. These include, as preferences, Lewis acids, for example boron trifluoride, boron trichloride, tin tetrachloride or titanium tetrachloride; and organic bases, such as pyridine and piperidine; as well as, in particular, piperidine acetate.

The reaction temperatures can be varied within a relatively wide range in carrying out process variant (b). In general, the reaction is carried out between $20°$ and $160°$ C., preferably at the boiling point of the particular solvent.

In carrying out process variant (b), 1 to 1.5 moles of aldehyde of the formula (V) and catalytic to 0.2 molar amounts of catalyst are employed per mole of triazolylketone of the formula (IV). The compounds of the formula (I) are isolated in the customary manner.

The following acids can preferably be used for the preparation of physiologically acceptable acid addition salts of the compounds of the formula (I): hydrogen halide acids (for example hydrobromic acid and, in particular, hydrochloric acid), phosphoric acid, nitric acid, sulphuric acid, monofunctional and bifunctional carboxylic acids and hydroxycarbonxylic acids (for example acetic acid, maleic acid, succinic acid, fumaric acid, tartaric acid, citric acid, salicylic acid, sorbic acid and lactic acid) and sulphonic acids (for example p-toluenesulphonic acid and 1,5-naphthalenedisulphonic acid).

The acid addition salts of the compounds of the formula (I) can be obtained in a simple manner by customary salt formation methods, for example by dissolving a compound of the formula (I) in a suitable inert solvent and adding the acid, for example hydrogen chloride, and they can be isolated in a known manner, for example by filtration, and if appropriate purified by washing with an inert organic solvent.

Salts of metlas of main groups II to IV and of subgroups I and II and IV to VIII are preferably used for the preparation of metal salt complexes of the compounds of the formula (I), examples of metals which may be mentioned being copper, zinc, manganese, magnesium, tin, iron and nickel.

Possible anions of the salts are preferably those which are derived from the following acids: hydrogen halide acids (for example hydrochloric acid and hydrobromic acid), phosphoric acid, nitric acid and sulphuric acid. The metal salt complexes of the compounds of the formula (I) can be obtained in a simple manner by customary processes, for example by dissolving the metal salt in alcohol, for example ethanol, and adding the solution to the compound of the formula (I). The metal salt complexes can be purified in a known manner, for example by filtration, isolation and, if appropriate, recrystallization.

The active compounds according to the invention exhibit a powerful microbicidal action and can be employed in practice for combating undersired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds which can be used according to the invention can be employed with particularly good success for combating those fungi which cause powdery mildew diseases, especially for combating Erysiphe species, for example against the powdery mildrew of barley or of cereal causative organism (*Erysiphe graminis*) and the powdery mildrew of cucumber causative organism (*Erysiphe cichoracearum*), and for combating Podosphaera species, such as against the powdery mildew of apple causative organism (*Podosphaera leucotricha*).

It should be particularly emphasised that the active compounds according to the invention have not only a protective action but also a systemic action. Thus, it is possible to protect plants from fungal attack if the active compound is fed to the above-ground parts of the plants via the soil and the roots or via the seed.

The active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liuid diluents or carriers, especially solvents, there are suitable in the main, aromatic hydrocarbons, such as xylene, toluene or alkyl naphthalenes, chlorinated aromatic or chlorinated aliphatic hydrocarcarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carries are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and inorganic meals, and granules of organic material such as sawdust, coconut shells, corn cobs and tobacco stalks.

As emulsifying and/or foam-forming agents there may be used non-ionic and anionic emulsifers, such as polyoxy-ethylene-fatty acid esters, polyoxyethlene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethlcellulose and natural and synthetic polymers in the form of powders, granules or latices, such as gum arabic, polyvinyl alcohol and polyvinyl acetates, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repllents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of in general 0.001 to 50 g, preferably 0.01 to 10 g, are employed per kilogram or seed.

For the treatment of soil, active compound concentrations of in general 0.00001 to 0.1% by weight, preferably 0.0001 to 0.02%, are required at the place of action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

EXAMPLE 1

Process variant (a)

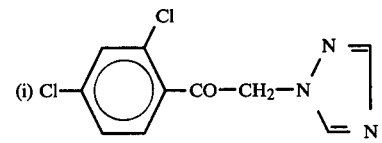

269 g (1mole) of ω-bromo-2,4-dichloroacetophenone were dissolved in 250 ml of acetonitrile. This solution was added dropwise to a suspension, boiling under reflux, of 69 g (1 mole) of 1,2,4-triazole and 150 g of potassium carbonate in 2,000 ml of acetonitrile. After heating the mixture under reflux for 18 to 24 hours, the cooled suspension was filtered, the filtrate was freed from the solvent, the residue was taken up with ethyl acetate and the ethyl acetate mixture was washed with water, dried over sodium sulphate and freed from the solvent. The residue from the ethyl acetate mixture crystallized out when isopropanol was added. After recrystallizing the product from ligroin/isopropanol, 154 g (60% of theory) of ω-(1,2,4-triazol-1-yl)-2,4-dichloroacetophenone of melting point 117° C. were obtained.

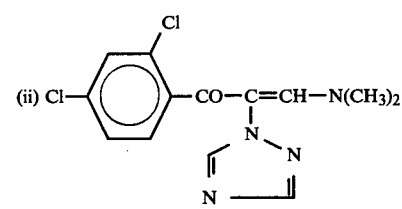

266 g (1 mole) of ω-(1,2,4-triazol-1-yl)-2,4-dichloro-acetophenone were heated under reflux with 131 g (1.1 mole) of dimethylformamide dimethylacetal for 5 hours. The excess acetal was then distilled off. The oil which remained crystallized on cooling. 292 g (94% of theory) of 1-(2,4-dichlorophenyl)-3-dimethylamino-2-(1,2,4-triazol-b 1-yl)-prop-2-en-1-one of melting point 173° C. were obtained.

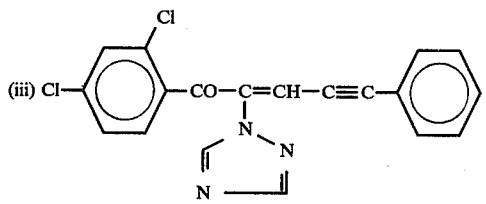
(1)

31.2 g (0.1 mole) of 1-(2,4-dichlorophenyl)-3-dimethyl-amino-2-(1,2,4-triazol-1-yl)-prop-2en-1-one were dissolved in 400 ml of tetrahydrofuran. A solution of 26.7 g (0.13 mole) of phenylacetylene-magnesium bromide in 70 ml of tetrahydrofuran was added dropwise to the solution at 31 10° C. in the course of 15 minutes. When the addition had ended, the reaction mixture was allowed to warm to room temperature in the course of about 2 hours. Dilute hydrochloric acid was then added and the organic phase was separated off, washed with water, dried over sodium sulphate and concentrated. 30 g (81.5% of theory) of 1-(2,4-dichlorophenyl)-5-phenyl-2-(1,2,4-triazol-1-yl)-pent-2-en-4-yn-1-one were obtained as an oil.

EXAMPLE 2

Process variant (b)

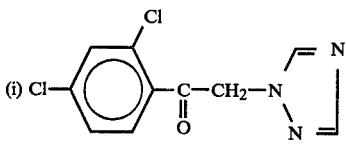

269 g (1 mole) of ω-bromo-2,4-dichloroacetophenone were dissolved in 250 ml of acetonitrile. This solution was added dropwise to a suspension, boiling under reflux, of 69 g (1 mole) of 1,2,4-triazole and 150 g of potassium carbonate in 2,000 ml of acetonitrile. After heating the mixture under reflux for 20 hours, the cooled suspension was filtered, the filtrate was freed from the solvent, the residue was taken up in ethyl acetate and the ethyl acetate mixture was washed with water, dried over sodium sulphate and freed from the solvent. The residue obtained from the ethyl acetate mixture crystallized out when isopropanol was added. After recrystallizing the product from ligroin/isopropanol, 154 g (60% of theory) of ω-(1,2,4-triazol-1-yl)-2,4-dichloroacetophenone of melting point 117° C. were obtained.

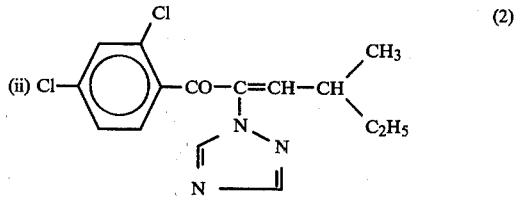
(2)

25.6 g (0.1 mole) of ω-(1,2,4-triazol-1-yl)-2,4-dichloro-acetophenone and 8.6 g (0.1 mole) of 2-methyl-butyraldehyde were heated under reflux together with 1 ml of piperidine and 1.5 ml of glacial acetic acid in 200 ml of toluene, using a water separator, until the theoretical amount of water (1.8 ml) had been removed. After cooling, the reaction solution was washed with saturated sodium chloride solution, the organic phase was separated off, dried over sodium sulphate and filtered and the filtrate was concentrated. The oily residue was taken up in hot ligroin, from which a colorless crystalline solid precipitated on cooling. 17.2 g (53.2% of theory) of 1-(2,4-dichlorophenyl)-4-methyl-2-(1,2,4-triazol-1-yl)-hex-2-en-1-one of melting point 101°–104° C. were obtained.

The following compounds of the general formula

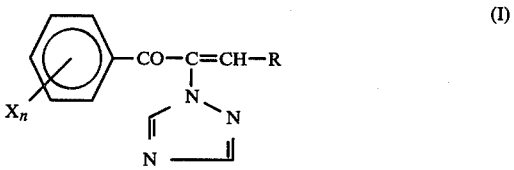
(I)

were obtained analogously:

TABLE 1

| Compound No. | $X_n$ | R | Melting point (°C.) Refractive index ($n_D^{20}$) |
| --- | --- | --- | --- |
| 3 | 2,4-Cl$_2$ | CH$_3$ | 105–07 |
| 4 | 2,4-Cl$_2$ | C$_2$H$_5$ | Oil |
| 5 | 2,4-Cl$_2$ | i-C$_3$H$_7$ | 63–67 |
| 6 | 2,4-Cl$_2$ | C(CH$_3$)$_3$ | 155–57 |
| 7 | 2,4-Cl$_2$ | n-C$_7$H$_{15}$ | 1,5320 |
| 8 | 2,4-Cl$_2$ | —CH(CN)—⌬—Cl | 180–85 |
| 9 | 4-Br | CH$_3$ | Oil |
| 10 | 4-Br | C$_2$H$_5$ | Oil |
| 11 | 4-Br | n-C$_4$H$_9$ | Oil |
| 12 | 4-O—⌬—Cl | C$_2$H$_5$ | 1,6080 |

TABLE 1-continued

| Compound No. | $X_n$ | R | Melting point (°C.) Refractive index ($n_D^{20}$) |
|---|---|---|---|
| 13 | 4-O—⟨C₆H₄⟩—Cl | CH₃ | 1,6188 |
| 14 | 4-Cl | —CH₂—⟨C₆H₅⟩ | 1,6112 |
| 15 | 2-Cl; 4-C(CH₃)₃ | C(CH₃)₃ | Oil |
| 16 | 4-Br | n-C₇H₁₅ | Oil |
| 17 | 2,4-Cl₂ | —CH₂—C(CH₃)=CH₂ | 1,5724 |
| 18 | 4-Cl | CH₃ | 1,5987 |
| 19 | 4-Cl | —C≡C—⟨C₆H₅⟩ | 120–23 |
| 20 | 4-Cl | C₂H₅ | 1,5812 |
| 21 | 2,4-Cl₂ | n-C₄H₉ | 1,5672 |
| 22 | 2,4-Cl₂ | n-C₄H₉ | 101–05(× CuCl₂) |
| 23 | 2,4-Cl₂ | n-C₇H₁₅ | Oil(× CuCl₂) |
| 24 | 2,4-Cl₂ | i-C₃H₇ | 96–99(× CuCl₂) |
| 25 | 2,4-Cl₂ | CH₃ | 98–102(× CuCl₂) |
| 26 | 2,4-Cl₂ | C₂H₅ | 83(× CuCl₂) |
| 27 | 4-Br | n-C₇H₁₅ | Oil(× CuCl₂) |
| 28 | 4-Br | C₂H₅ | 82(× CuCl₂) |
| 29 | 4-O—⟨C₆H₄⟩—Cl | CH₃ | 85–90(× CuCl₂) |
| 30 | 4-Cl | —CH₂—⟨C₆H₅⟩ | 130–33(× CuCl₂) |
| 31 | 4-Cl | C₂H₅ | 92–94(× CuCl₂) |
| 32 | 2,4-Cl₂ | —CH(CH₃)—C₂H₅ | 88–92(× CuCl₂) |
| 33 | 2,4-Cl₂ | ⟨cyclohexenyl⟩ | 105 |
| 34 | 2,4-Cl₂ | —CH(C₂H₅)—C₄H₉—n | 73 |
| 35 | 2,4-Cl₂ | —CH(C₂H₅)₂ | 88 |
| 36 | 2,4-Cl₂ | ⟨cyclohexyl-CH₃⟩ | Oil |
| 37 | 2,4-Cl₂ | ⟨cyclohexyl-H⟩ | Oil |
| 38 | 2,4-Cl₂ | —CH(CH₃)—C₃H₇—n | Oil |
| 39 | 4—⟨C₆H₅⟩ | —CH(C₂H₅)—C₄H₉—n | Oil |
| 40 | 4-F | —CH(CH₃)—C₂H₅ | Oil |
| 41 | 4—⟨C₆H₅⟩ | —CH(CH₃)—C₂H₅ | Oil |
| 42 | 4-F | —CH(C₂H₅)—C₄H₉—n | Oil |
| 43 | 4—⟨C₆H₄⟩—Cl | —CH(CH₃)₂ | 84 |
| 44 | 4—⟨C₆H₄⟩—Cl | —CH(C₂H₅)—C₄H₉—n | Oil |
| 45 | 4—⟨C₆H₄⟩—Cl | ⟨cyclohexenyl⟩ | Oil |

TABLE 1-continued

| Compound No. | $X_n$ | R | Melting point (°C.) Refractive index ($n_D^{20}$) |
|---|---|---|---|
| 46 | 4-⟨C₆H₄⟩-Cl | —CH(C₂H₅)₂ | Oil |
| 47 | 2,4-Cl₂ | —⟨C₆H₄⟩—O—⟨C₆H₅⟩ | Oil |
| 48 | 4-Cl | —CH₃ | 138(× CuCl₂) ELB 1096 |
| 49 | 4-Cl | —C≡C—⟨C₆H₅⟩ | 90(× CuCl₂) ELB 1250 |

The fungicidal activity of the compounds of this invention is illustrated by the following biological examples wherein the compounds according to the present invention are each identified by the number (given in brackets) from Examples 1 and 2 and Table 1 hereinabove:

The known comparsion compounds are identified as follows:

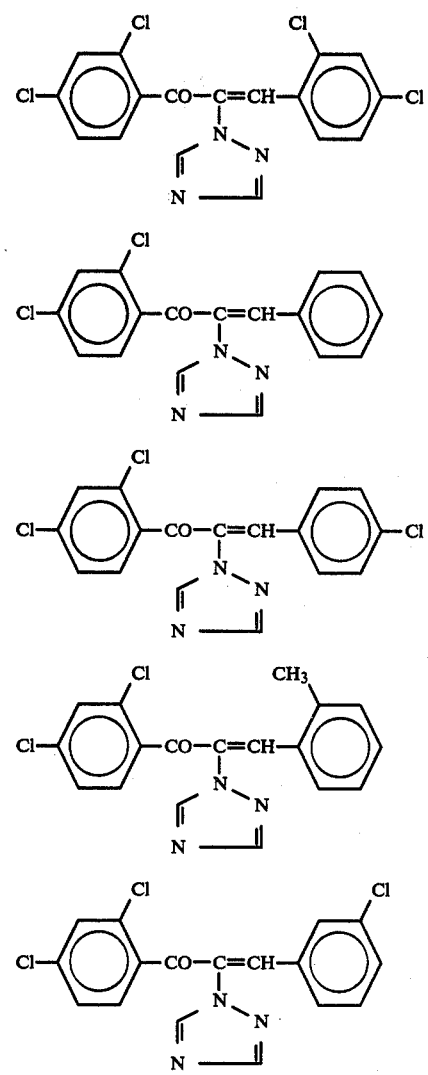

EXAMPLE 3

Erysiphe test (barley)/protective

Solvent: 100 parts by weight of dimethylformamide
Emulsifier: 0.25 part by weight of alkylarylpolyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dew-moist. After the spray coating had dried on, the plants were dusted with spores of *Erysiphe graminis* f.sp. hordei.

The plants were placed in a greenhouse at a temperature of about 20° C. and a relative atmospheric humidity of about 80%, in order to promote the development of powdery mildew pustules.

Evaluation was carried out 7 days after the inoculation.

In this test, a clearly superior activity compared with the prior art was shown, for example, by the compounds (3), (6), (5), (32), (25), (24), (34), (35), (2), (43), and (46), as can be seen from the following test results:

TABLE 2

Erysiphe test (barley)/protective

| Active compound | Active compound concentration in the spray liquor in % by weight | Disease infestation in % of the untreated control |
|---|---|---|
| (A) | 0.0025 | 75.0 |
| (B) | 0.0025 | 83.8 |
| (3) | 0.0025 | 33.8 |
| (6) | 0.0025 | 0.0 |
| (5) | 0.0025 | 12.5 |
| (32) | 0.0025 | 0.0 |
| (25) | 0.0025 | 33.8 |
| (24) | 0.0025 | 13.8 |
| (34) | 0.0025 | 25.0 |
| (35) | 0.0025 | 0.0 |
| (2) | 0.0025 | 21.3 |
| (43) | 0.0025 | 25.0 |
| (46) | 0.0025 | 33.8 |

EXAMPLE 4

Powdery mildew of barley test (*Erysiphe graminis* var. hordei)/systemic (fungal disease of cereal shoots).

The acitve compounds were used as pulverulent seed treatment agents. These were produced by extending the active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was sown at the rate of 3×12 grains in flowerpots, 2 cm deep in a mixture of one part by volume of Fruhstorfer standard soil and one part by volume of quartz sand. The germination and emergence took place under favorable conditions in a greenhouse. 7 days after sowing, when the barley plants has unfolded their first leaf, they were dusted with fresh spores of *Erysiphe graminis* var. hordei and grown on at 21°–22° C. and 80–90% relative atmospheric humidity and 16 hours' exposure to light. The typical mildew pustules formed on the leaves within 6 days.

The degree of infection was expressed as a percentage of the infection of the untreated control plants. Thus, 0% denoted no infection and 100% denoted the same degree of infection as in the case of the untreated control. The active compound was the more active, the lower was the degree of mildew infection.

In this test, a clearly superior activity compared with the prior art was shown, for example, by the compounds (5), (32), (35) and (2), as can be seen from the following test results:

TABLE 3

Powdery mildew of barley test (*Erysiphe graminis* var. hordei)/systemic

| Active compounds | Active compound concentraton in the dressing agent in % by weight | Amount of dressing agent applied in g/kg of seed | Infection in % of the untreated control |
|---|---|---|---|
| (C) | 25 | 10 | 100 |
| (D) | 25 | 10 | 100 |
| (5) | 25 | 4 | 0.0 |
| (32) | 25 | 4 | 0.0 |
| (35) | 25 | 10 | 16.3 |
| (2) | 25 | 10 | 0.0 |

EXAMPLE 5

Erysiphe test (cucumbers)/protective

Solvent: 4.7 parts by weight of acetone
Emulsifier: 0.3 part by weight of alkylaryl polyglycol ether
Water: 95.0 parts by weight The amount of active compound required for the desired concentration of active compound in the spray liquid was mixed with the stated amount of solvent, and the concentrate was diluted with the stated amount of water which contained the stated additions.

Young cucumber plants with about three foliage leaves were sprayed with the spray liquid until dripping wet. The cucumber plants remained in a greenhouse for 24 hours to dry. They were then, for the purpose of inoculation, dusted with conidia of the fungus *Erysiphe cichoracearum*. The plants were subsequently placed in a greenhouse at 23° to 24° C. and at a relative atmospheric humidity of about 75%.

After 12 days, the infection of the cucumber plants was determined. The assessment data were converted to per cent infection. 0% denotes no infection and 100% meant that the plants are totally infected.

In this test, a clearly superior activity compared with the prior art was shown, for example, by the compounds (6), (32) and (35), as can be seen from the following test results.

TABLE 4

Erysiphe test (cucumbers)/protective

| Active compound | Infection in % at an active compound concentration of 0.0005% |
|---|---|
| (A) | 37 |
| (6) | 12 |
| (32) | 12 |
| (35) | 16 |

EXAMPLE 6

Podesphaera test (apple)/protective

Solvent: 4.7 parts by weight of acetone
Emulsifier: 0.3 part by weight of alkylaryl polyglycol ether
Water: 95.0 parts by weight The amounts of active compound required for the desired concentration of the active compound in the spray liquid was mixed with the stated amount of solvent, and the concentrate was diluted with the stated amount of water which contained the stated additions.

Young apple seedlings in the 4 to 5 leaf stage were sprayed with the spray liquid until dripping wet. The plants remained in a greenhouse for 24 hours at 20° C. and at a relative atmospheric humidity of 70%. They were then inoculated by dusting with conidia of the apple powdery mildew causative organism (*Podosphaera leucoticha*) and placed in a greenhouse at a temperature of 21° to 23° C. and at a relative atmospheric humidity of about 70°.

10 days after the inoculation, the infection of the seedlings was determined. The assessment data were converted to present infection. 0% denoted no infection and 100% denoted that the plants were totally infected.

In this test, a clearly superior activity compared with the prior art was shown, for example, by the compounds (6), (1), (5), (32), (25), (34), (2), (37), (38), (40), (43), (44) and (46), as can be seen from the following test results:

TABLE 5

Podosphaera test (apple)/protective

| Active compound | Infection in % at an active compound concentration of 0.001% |
|---|---|
| (D) | 76 |
| (E) | 37 |
| (6) | 0 |
| (1) | 30 |
| (5) | 1 |
| (32) | 0 |
| (25) | 17 |
| (34) | 7 |
| (37) | 24 |
| (2) | 1 |
| (38) | 1 |
| (40) | 22 |
| (43) | 16 |
| (44) | 15 |
| (46) | 5 |

It will be appreciated that the instant specification and examples are set forth by way of illustration and not limitation, and that various modifications and changes may be made without departing from the spirit and scope of the present invention.

We claim:

1. A 1-phenyl-2(1,2,4-triazol-1-yl)-prop-2-en-1-one of the formula

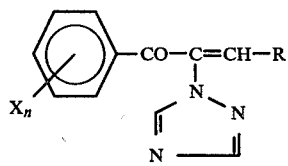

in which

R is phenylacetylene,

X is halogen, or phenyl or phenoxy either of which may optionally carry one or more substituents selected from halogen, alkyl with 1 to 4 carbon atoms and halogenoalkyl with 1 to 4 carbon atoms and 1 to 5 halogen atoms, and n is 0, 1, 2 or 3, or an addition product thereof with a physiologically acceptable acid or a metal salt.

2. A compound or addition product according to claim 1 of the formula

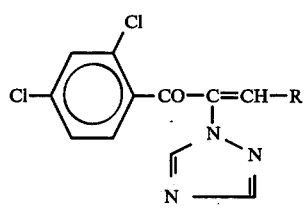

3. A compound or addition product according to claim 1, wherein such compound is 1-(2,4-dichlorophenyl)-5-phenyl-2-(1,2,4-triazol-1-yl)-pent-2-en-4-yn-1-one of the formula

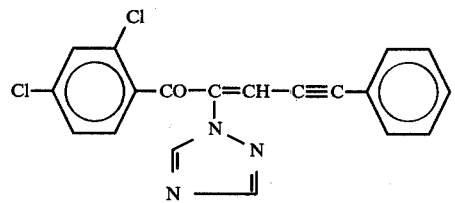

4. A compound or addition product according to claim 1, wherein such compound is 1-(4-chlorophenyl)-5-phenyl-2-(1,2,4-triazol-1-yl)-pent-2en-4-yn-1-one of the formula

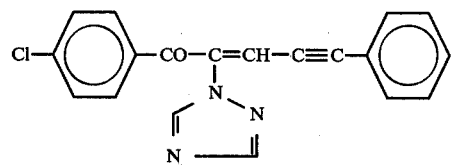

5. A fungicidal composition comprising a fungicidally effective amount of a compound of addition product thereof according to claim 1 in admixture with a diluent.

6. A method of combating fungi comprising applying to the fungi, or to a habitat thereof, a fungicidally effective amount of a compound or addition product thereof according to claim 1.

7. The method according to claim 6, wherein such compound is
1-(2,4-dichlorophenyl)-5-phenyl-2-(1,2,4-triazol-1-yl)-pent-2-en-4-yn-1-one or
1-(4-chlorophenyl)-5-phenyl-2-(1,2,4-triazol-1-yl)-pent-2-en-4-yn-1-one.

8. 1-(2,4-Dichlorophenyl)-4,4-dimethyl-2-(1,2,4-triazol-1-yl)-pent-2-en-1-one of the formula

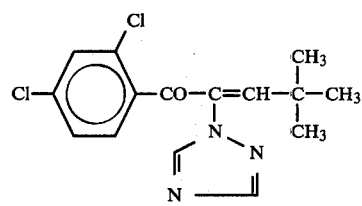

or an addition product thereof with a physiologically acceptable acid or a metal salt.

9. A fungicidal composition comprising a fungicidally effective amount of a compound or addition product thereof according to claim 8 in admixture with a diluent.

10. A method of combating fungi comprising applying to the fungi, or to a habitat thereof, a fungicidally effective amount of a compound or addition product thereof according to claim 8.

* * * * *

UNITED STATES PATENT AND TRADEMARK OFFICE
CERTIFICATE OF CORRECTION

PATENT NO. : 4,435,411

DATED : March 6, 1984

INVENTOR(S) : Wolf Reiser et al

Page 1 of 2

It is certified that error appears in the above-identified patent and that said Letters Patent is hereby corrected as shown below:

| | |
|---|---|
| Col. 2, line 1 | Delete "Hal-R" and substitute --Hal-Mg-R-- |
| Col. 3, line 17 | After "1" delete "to" and substitute --or-- |
| Col. 5, line 32 | Delete "discolorbenzene" and substitute --dichlorobenzene-- |
| Col. 6, line 3 | Delete "metlas" and substitute --metals-- |
| Col. 6, line 18 | Delete "complaxes" and substitute --complexes-- |
| Col. 6, line 41 | Delete "mildrew" and substitute --mildew-- |
| Col. 6, line 43 | Delete "mildrew" and substitute --mildew-- |
| Col. 7, line 3 | Delete "liuid" and substitute --liquid-- |
| Col. 7, line 32 | Delete "emulsifers" and substitute --emulsifiers-- |
| Col. 7, line 34 | Delete "polyoxyethlene" and substitute --polyoxyethylene-- |
| Col. 7, line 40 | Delete "carboxymethlcellulose" and substitute --carboxymethylcellulose-- |
| Col. 7, line 43 | Delete "acetates" and substitute --acetate-- |
| Col. 9, line 7 | Delete "-triazol-b 1-yl)" and substitute -- -triazol-1-yl)-- |
| Col. 9, line 20 | Between "2" and "en" insert -- - -- |

UNITED STATES PATENT AND TRADEMARK OFFICE
CERTIFICATE OF CORRECTION

PATENT NO. : 4,435,411
DATED : March 6, 1984
INVENTOR(S) : Wolf Reiser et al

It is certified that error appears in the above-identified patent and that said Letters Patent is hereby corrected as shown below:

Col. 9, line 24   Delete "31 10°" and substitute -- -10° --

Col. 16, line 18  Delete "Podesphaera" and substitute --Podosphaera--

Col. 18, line 13  Delete "-2en-" and substitute -- -2-en- --

Signed and Sealed this

Seventh Day of August 1984

[SEAL]

Attest:

Attesting Officer

GERALD J. MOSSINGHOFF
Commissioner of Patents and Trademarks